US00PP13031P2

(12) United States Plant Patent
Bergman

(10) Patent No.: US PP13,031 P2
(45) Date of Patent: Oct. 1, 2002

(54) CHRYSANTHEMUM PLANT NAMED 'YOCOVINGTON'

(75) Inventor: Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/955,688

(22) Filed: Sep. 20, 2001

(51) Int. Cl.[7] ..... A01H 5/00
(52) U.S. Cl. ..... Plt./289

(58) Field of Search ..... Plt./289

*Primary Examiner*—Anne Marie Grünberg
(74) *Attorney, Agent, or Firm*—C. A. Whealy

(57) ABSTRACT

A distinct cultivar of Chrysanthemum plant named 'Yocovington', characterized by its uniform and compact plant habit; strong and freely branching growth habit; dense dark green foliage; uniform and freely flowering habit; early flowering, seven-week response time; large decorative-type inflorescences that are about 11.4 cm in diameter; bright yellow-colored ray florets; good postproduction longevity with plants maintaining good substance and color for about three to four weeks in an interior environment; and tolerance to high production temperatures.

2 Drawing Sheets

BACKGROUND OF THE INVENTION

The present Invention relates to a new and distinct cultivar of Chrysanthemum plant, botanically known as *Chrysanthemum×morifolium* and hereinafter referred to by the name 'Yocovington'.

The new Chrysanthemum is a product of a planned breeding program conducted by the Inventor in Fort Myers, Fla. and Salinas, Calif. The objective of the breeding program is to create new potted Chrysanthemum cultivars that are suitable for year-round production with uniform plant growth habit, good vigor, desirable inflorescence form and floret colors, fast response time, and good postproduction longevity.

The new Chrysanthemum originated from a cross made by the Inventor in February, 1997, in Salinas, Calif., of a proprietary Chrysanthemum seedling selection identified as code number YB-4620, not patented, as the female, or seed, parent with a proprietary Chrysanthemum seedling selection identified as code number YB-6145, not patented, as the male, or pollen, parent. The new Chrysanthemum was discovered and selected by the Inventor as single flowering plant within the progeny of the stated cross grown in a controlled environment in Salinas, Calif. The selection of this plant was based on its uniform plant growth habit, desirable inflorescence form and floret colors, fast response time, and excellent postproduction longevity.

Asexual reproduction of the new Chrysanthemum by vegetative tip cuttings was first conducted in Fort Myers, Fla. in July, 1998. Asexual reproduction by cuttings has shown that the unique features of this new Chrysanthemum are stable and reproduced true to type in successive generations.

SUMMARY OF THE INVENTION

The cultivar Yocovington has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'Yocovington'. These characteristics in combination distinguish 'Yocovington' as a new and distinct Chrysanthemum:

1. Uniform and compact plant habit.
2. Strong and freely branching growth habit.
3. Dense dark green foliage.
4. Uniform and freely flowering habit.
5. Can be grown as a disbud or spray-type.
6. Early flowering, seven-week response time.
7. Large decorative-type inflorescences that are about 11.4 cm in diameter.
8. Bright yellow-colored ray florets.
9. Good postproduction longevity with plants maintaining good substance and color for about three to four weeks in an interior environment.
10. Tolerant to high production temperatures.

Plants of the new Chrysanthemum differ primarily from plants of the female parent selection in ray floret coloration as plants of the new Chrysanthemum have bright yellow ray florets wheras plants of the female parent selection have light bronze ray florets.

Compared to plants of the male parent selection, plants of the new Chrysanthemum have brighter yellow-colored ray florets and flower about one week earlier.

Plants of the new Chrysanthemum can be compared to plants of the cultivar McCahon's Yellow 11-90, disclosed in U.S. Plant Pat. No. 8,443. In side-by-side comparisons conducted by the Inventor in Salinas, Calif., plants of the new Chrysanthemum differed from plants of the cultivar McCahon's Yellow 11-90 in the following characteristics:

1. Plants of the new Chrysanthemum had shorter internodes and appeared denser and bushier than plants of the cultivar McCahin's Yellow 11-90.

2. Plants of the new Chrysanthemum flowered about one week earlier than plants of the cultivar McCahon's Yellow 11-90.

3. Ray floret color of plants of the new Chrysanthemum was brighter yellow than ray floret color of plants of the cultivar McCahon's Yellow 11-90.

4. Plants of the new Chrysanthemum were more high temperature tolerant than plants of the cultivar McCahon's Yellow 11-90.

Plants of the new Chrysanthemum can also be compared to plants of the cultivar Yellow Yosierra, disclosed in U.S. Plant Pat. No. 12,247. In side-by-side comparisons conducted by the Inventor in Salinas, Calif., plants of the new Chrysanthemum differed from plants of the cultivar Yellow Yosierra in the following characteristics:

1. Plants of the new Chrysanthemum had darker green foliage than plants of the cultivar Yellow Yosierra.

2. Plants of the new Chrysanthemum flowered about one week earlier than plants of the cultivar Yellow Yosierra.

3. Ray floret color of plants of the new Chrysanthemum was brighter yellow than ray floret color of plants of the cultivar Yellow Yosierra.

4. Plants of the new Chrysanthemum were much more high temperature tolerant than plants of the cultivar Yellow Yosierra.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type. Colors in the photographs may differ from the color values cited in the detailed botanical description which accurately describe the colors of the new Chryanthemum.

The photograph on the first sheet comprises a side perspective view of a typical flowering plant of 'Yocovington' grown as a disbud-type.

The photograph on the second sheet comprises a close-up view of typical inflorescences of 'Yocovington' grown as a disbud-type.

DETAILED BOTANICAL DESCRIPTION

In the following description, color references are made to The Royal Horticultural Society Colour Chart except where general terms of ordinary dictionary significance are used. The following observations and measurements describe plants grown and flowered during the summer in Salinas, Calif., in a fiberglass-covered greenhouse and under conditions which approximate those generally used in commercial potted Chrysanthemum production. During the production of these plants, the following conditions were measured: day temperatures, 21 to 27° C.; night temperatures, 17 to 19° C.; and light levels, 5,000 to 6,000 foot-candles. Four unrooted cuttings were directly stuck in 15-cm containers, exposed to long day/short night conditions, and pinched once about 14 days later. One week after pinching, the photoinductive short day/long night treatments were started. Plants used for this description were grown as disbud-types. Measurements and numerical values represent averages of typical flowering plants.

Botanical classification: *Chrysanthemum×morifolium* cultivar Yocovington.

Commercial classification: Decorative-type potted Chrysanthemum.

Parentage:

*Female, or seed, parent.*—Proprietary *Chrysanthemum×morifolium* seedling selection identified as code number YB-4620, not patented.

*Male, or pollen, parent.*—Proprietary *Chrysanthemum×morifolium* seedling selection identified as code number YB-6145, not patented.

Propagation:

*Type.*—Terminal tip cuttings.

*Time to initiate roots.*—About four days at 21° C.

*Time to produce a rooted cutting.*—About ten days at 21° C.

*Root description.*—White, fibrous.

*Rooting habit.*—Freely branching.

Plant description:

*Appearance.*—Herbaceous decorative-type potted Chrysanthemum that can be grown as a disbud or as a spray-type. Stems mostly upright and somewhat outwardly spreading; uniform crown. Very freely branching, about five lateral branches develop after removal of terminal apex (pinching); dense and full plants.

*Plant height.*—About 28.5 cm.

*Plant width.*—About 46 cm.

*Lateral branches (peduncles).*—Length: About 22 cm. Diameter: About 4.5 mm. Internode length: About 1.6 cm. Strength: Strong. Texture: Pubescent. Color: 146A.

*Foliage description.*—Arrangement: Alternate. Quantity of leaves per lateral stem: About 11 or 12. Length: About 7.8 cm. Width: About 6.3 cm. Apex: Cuspidate to mucronate. Base: Attenuate to truncate. Margin: Palmately lobed, sinuses between lateral lobes parallel to divergent. Texture: Upper and lower surfaces with very fine pubescence; veins prominent on lower surface. Color: Young and mature foliage, upper surface: Darker than 147A. Young and mature foliage, lower surface: Darker than 147B. Venation, upper surface: Close to 146C. Venation, lower surface: 147B to 146C. Petiole length: About 2.5 cm. Petiole diameter: About 3 mm. Petiole color, both surfaces: Close to 146B to 146C.

Inflorescence description:

*Appearance.*—Decorative-type inflorescence form with elongated oblong-shaped ray florets. Inflorescences borne on terminals above foliage. Disk and ray florets arranged acropetally on a capitulum. Not fragrant. Can be grown as a disbud or spray-type.

*Flowering response.*—Under natural conditions, plants flower in the autumn/winter in the Northern Hemisphere. At other times of the year, inflorescence initiation and development can be induced under short day/long night conditions (at least 13.5 hours of darkness). Early flowering; plants exposed to three weeks of long day/short night conditions followed by photoinductive short day/long night conditions flower about 46 to 50 days later.

*Postproduction longevity.*—Inflorescences maintain good color and substance for about three to four weeks in an interior environment.

*Quantity of inflorescences.*—Grown as a disbud-type, only one inflorescence, the terminal inflorescence, develops per lateral branch.

*Inflorescence bud.*—Height: About 7 mm. Diameter: About 1 cm. Color: Closest to 137A.

*Inflorescence size.*—Diameter: About 11.4 cm. Depth (height): About 3.2 cm. Diameter of disc: About 7 mm. Receptacle diameter: About 1.25 cm.

*Ray florets.*—Shape: Elongated-oblong. Orientation: Initially upright, then perpendicular to the peduncle. Aspect: Initially incurved, then slightly concave. Length: About 5.6 cm. Width: About 1.6 cm. Apex: Rounded or emarginate. Base: Attenuate. Corolla tube length: About 1 cm. Margin: Entire. Texture: Smooth, glabrous, satiny. Number of ray florets per inflorescence: About 225 arranged in numerous rows. Color: When opening and fully expanded, upper surface: 5A to 7A. When opening and fully expanded, lower surface: 8A to 8B.

*Disc florets.*—Arrangement: Massed at center of receptacle. Shape: Tubular, elongated. Apex: Five-pointed. Length: About 7.5 mm. Width: Apex: About 1.5 mm. Base: About 1 mm. Number of disc florets per inflorescence: About 25. Color: Immature: 154A. Mature: Apex: 7A. Mid-section: Close to 145C. Base: 155D.

*Reproductive organs.*—Androecium: Present on disc florets only. Anther color: 9A. Pollen amount: Scarce. Pollen color: 12A. Gynoecium: Present on both ray and disc florets.

*Seed.*—Seed production has not been observed.

Disease resistance: Resistance to pathogens common to Chrysanthemums has not been observed on plants grown under commercial greenhouse conditions.

High temperature tolerance: Plants of the new Chrysanthemum have been observed to be tolerant to high temperature conditions when grown during the summer under greenhouse conditions in southwest Florida.

It is claimed:

1. A new and distinct cultivar of Chrysanthemum plant named 'Yocovington', as illustrated and described.

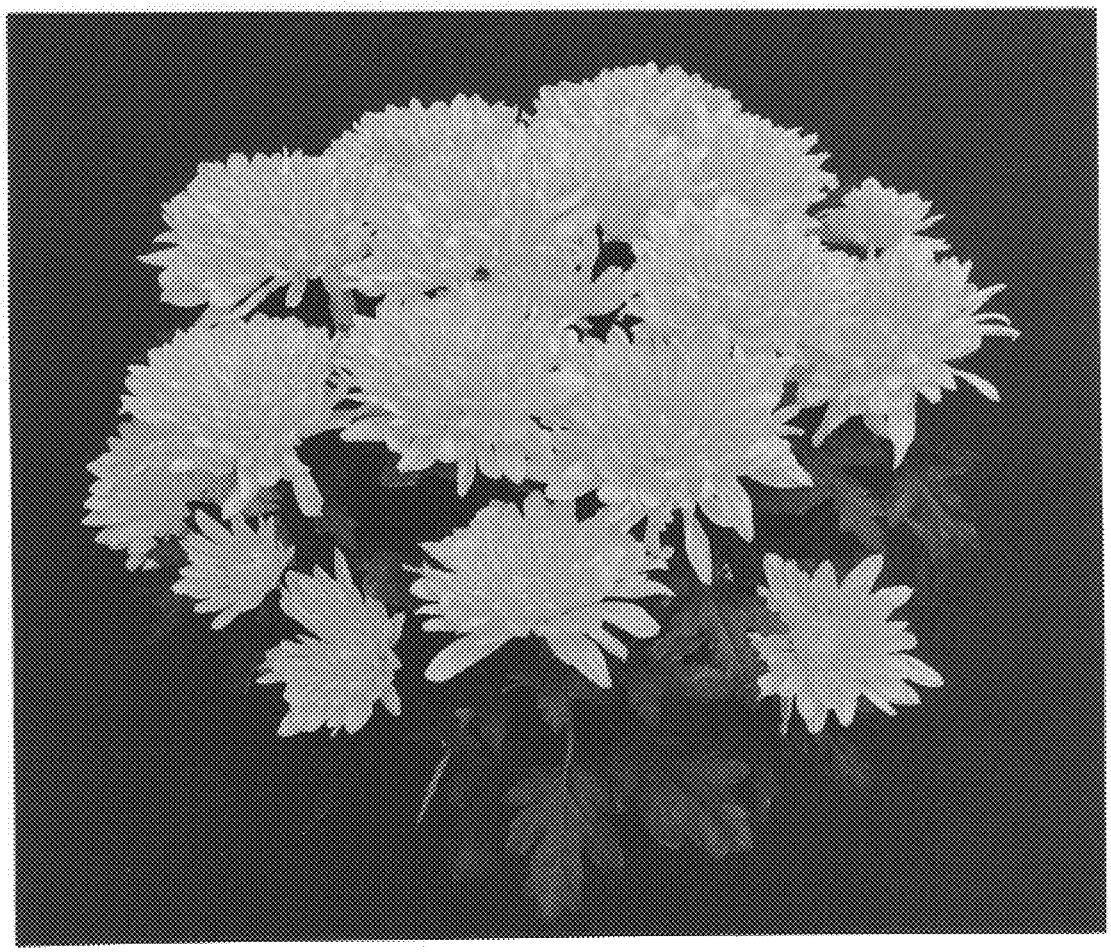

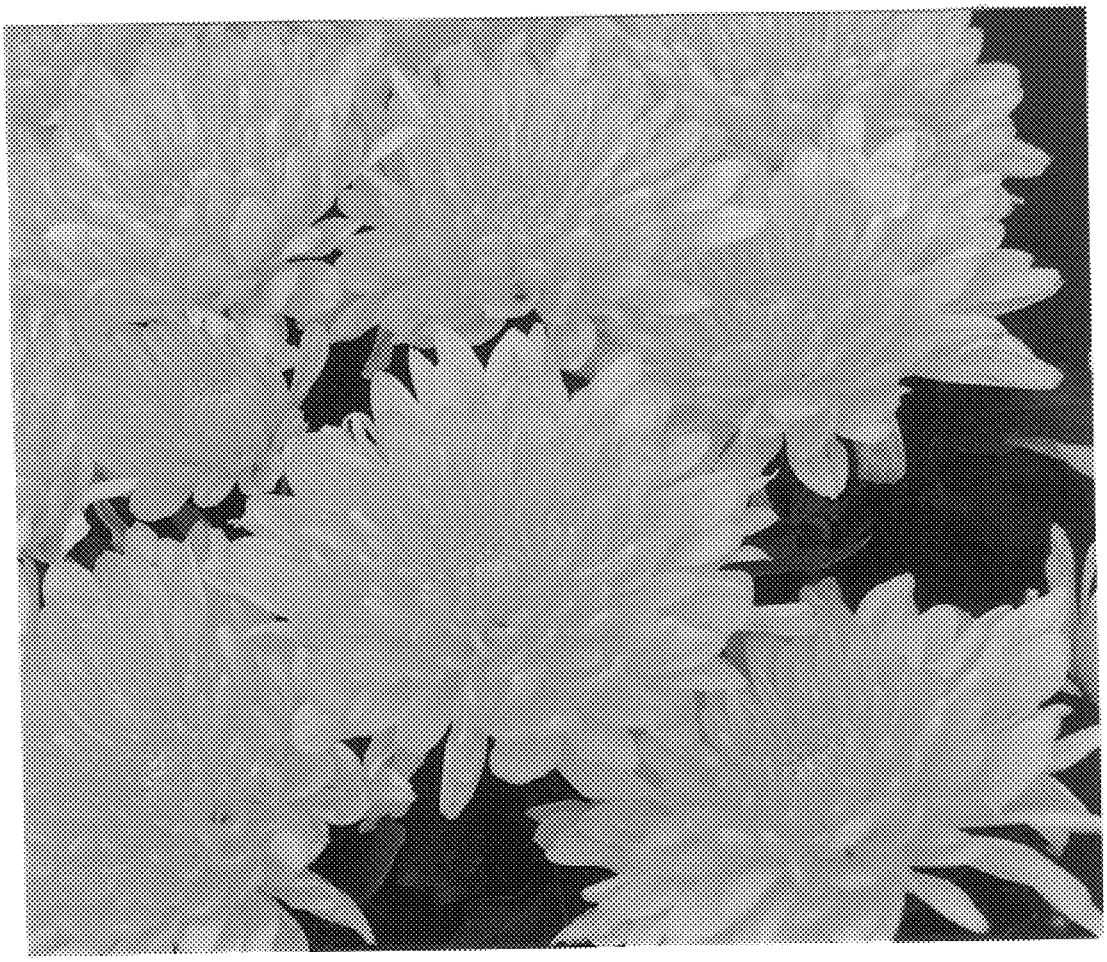

* * * * *